United States Patent
Naidu et al.

(10) Patent No.: US 7,173,022 B2
(45) Date of Patent: Feb. 6, 2007

(54) BICYCLIC HETEROCYCLES AS HIV INTEGRASE INHIBITORS

(75) Inventors: B. Narasimhulu Naidu, Durham, CT (US); Jacques Banville, St-Hubert (CA); John D. Matiskella, Wallingford, CT (US); Serge Plamondon, Ste-Catherine (CA); Yasutsugu Ueda, Clinton, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/138,773

(22) Filed: May 26, 2005

(65) Prior Publication Data

US 2005/0267131 A1    Dec. 1, 2005

Related U.S. Application Data

(60) Provisional application No. 60/603,371, filed on Aug. 20, 2004, provisional application No. 60/575,513, filed on May 28, 2004.

(51) Int. Cl.
| | |
|---|---|
| A61K 31/517 | (2006.01) |
| A61K 31/55 | (2006.01) |
| C07D 239/74 | (2006.01) |
| C07D 487/04 | (2006.01) |
| A61P 31/18 | (2006.01) |
| C07D 249/08 | (2006.01) |
| C07D 211/94 | (2006.01) |
| C07D 498/04 | (2006.01) |

(52) U.S. Cl. .............. 514/214.02; 544/282; 514/259.5; 540/579; 546/244; 546/115; 548/267.4

(58) Field of Classification Search ........... 514/214.02, 514/259.5, 259.2; 540/593, 579; 544/282
See application file for complete search history.

(56) References Cited

U.S. PATENT DOCUMENTS

2004/0006065 A1   1/2004   Glunz

FOREIGN PATENT DOCUMENTS

| WO | WO 2003/035076 A1 | 5/2003 |
| WO | WO 2003/035077 A1 | 5/2003 |
| WO | WO 2004/058756 A1 | 7/2004 |
| WO | WO 2004/058757 A1 | 7/2004 |
| WO | WO 2005/061490 A1 | 7/2005 |
| WO | WO 2005/061501 A2 | 7/2005 |

OTHER PUBLICATIONS

West, Anthony R., Solid State Chemistry and its Applications, Wiley, New York, 1988, pp. 358 & 365.*

* cited by examiner

*Primary Examiner*—Mark Berch
*Assistant Examiner*—Susanna Moore
(74) *Attorney, Agent, or Firm*—James Epperson

(57) ABSTRACT

The invention encompasses a series cyclic bicyclic heterocyclic compounds of Formula I which are inhibitors of HIV integrase and prevent viral integration into human DNA. This action makes the compounds useful for treating HIV infection and AIDS. The invention also encompasses pharmaceutical compositions and methods for treating those infected with HIV

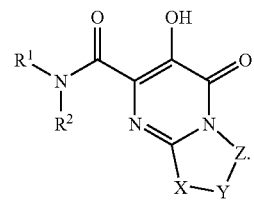

14 Claims, No Drawings

BICYCLIC HETEROCYCLES AS HIV INTEGRASE INHIBITORS

CROSS REFERENCE TO RELATED APPLICATIONS

This application claims the benefit of U.S. Provisional Application Ser. No. 60/603,371 filed Aug. 20, 2004 and 60/575,513 filed May 28, 2004.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into three classes based on the viral protein they target and their mode of action. In particular, saquinavir, indinavir, ritonavir, nelfinavir and amprenavir are competitive inhibitors of the aspartyl protease expressed by HIV. Zidovudine, didanosine, stavudine, lamivudine, zalcitabine and abacavir are nucleoside reverse transcriptase inhibitors that behave as substrate mimics to halt viral cDNA synthesis. The non-nucleoside reverse transcriptase inhibitors, nevaripine, delavirdine and efavirenz inhibit the synthesis of viral cDNA via a non-competitive (or uncompetitive) mechanism. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Further, J.; Satten, G. A.; Aschman, D. J.; Holmberg, S. D. *N. Engl. J. Med.* 1998, 338, 853–860).

Unfortunately, not all patients are responsive and a large number fail this therapy. In fact, approximately 30–50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/mL) (Carpenter, C. C.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schechter, M.; Schooley, R. T.; Thompson, M. A.; Vella, S.; Yeni, P. G.; Volberding, P. A. *JAMA* 2000, 283, 381–390). Clearly there is a need for new antiviral agents, preferably targeting other viral enzymes to reduce the rate of resistance and suppress viral replication even further.

HIV expresses three enzymes, reverse transcriptase, an aspartyl protease, and integrase. All three are targets for treating AIDS and HIV infection. HIV integrase catalyzes insertion of the viral cDNA into the host cell genome, which is a critical step in the viral life cycle. HIV integrase inhibitors belonging to a class of diketo acid compounds prevented viral integration and inhibited HIV-1 replication in cells (Hazuda et al. *Science* 2000, 287, 646). And recently, HIV integrase inhibitors have been accepted into clinical trials for treating AIDS and HIV infection (Neamati *Expert. Opin. Ther. Patents* 2002, 12, 709, Pais and Burke *Drugs Fut.* 2002, 27, 1101).

DESCRIPTION OF THE INVENTION

The invention encompasses compounds of Formula I, including pharmaceutically acceptable salts and solvates, their pharmaceutical compositions, and methods for inhibiting HIV integrase and treating those infected with HIV.

One aspect of the invention is a compound of Formula I

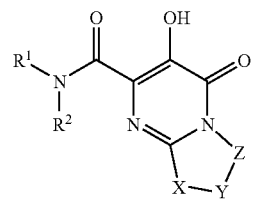

wherein:

$R^1$ is $C_{1-6}(Ar^1)$alkyl;

$R^2$ is hydrogen, hydroxy, $C_{1-6}$alkyl, or $C_{1-6}$alkoxy;

$R^3$ is hydrogen, halo, hydroxy, cyano, $C_{1-6}$alkyl, $C_{1-6}$haloalkyl, $C_{1-6}$alkoxy, $C_{1-6}$haloalkoxy, $CON(R^6)(R^6)$, or $Ar^2$;

$R^4$ is hydrogen, halo, hydroxy, cyano, $C_{1-6}$alkyl, $C_{1-6}$alkoxy, $C_{1-6}$haloalkyl, or $C_{1-6}$haloalkoxy;

$R^5$ is hydrogen, halo, hydroxy, cyano, $C_{1-6}$alkyl, $C_{1-6}$alkoxy, $C_{1-6}$haloalkyl, or $C_{1-6}$haloalkoxy;

$R^6$ is hydrogen or $C_{1-6}$alkyl;

$R^7$ is $C_{1-6}$alkyl;

$Ar^1$ is

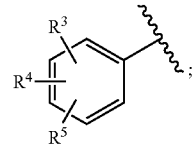

$Ar^2$ is tetrazolyl, triazolyl, pyrazolyl, imidazolyl, pyrrolyl, or dixothiazinyl, and is substituted with 0–2 substituents selected from the group consisting of amino, oxo, halo, and $C_{1-6}$alkyl;

$Ar^3$ is phenyl or pyridinyl substituted with 0–2 substituents selected from halo, $C_{1-6}$alkyl, and $C_{1-6}$alkoxy; and X—Y—Z is $C(R^7)_2CH_2CH_2$, $C(R^7)_2CH_2CH_2CH_2$, $C(R^7)_2CH_2CH_2CH_2CH_2$, $C(Ar^3)$=$CHCH_2$, $C(Ar^3)$=$CHCH_2CH_2$, or $C(Ar^3)$=$CHCH_2CH_2CH_2$;

or a pharmaceutically acceptable salt or solvate thereof.

Another aspect of the invention is a compound of Formula I where $R^1$ is

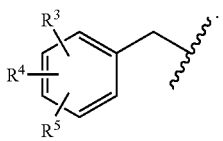

Another aspect of the invention is a compound of Formula I where $R^1$ is

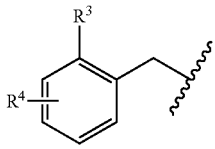

Another aspect of the invention is a compound of Formula I where $R^2$ is hydrogen.

Another aspect of the invention is a compound of Formula I where $R^3$ is hydrogen, chloro, flouro, methyl, or $NHCOR^6$; $R^4$ is hydrogen, chloro, flouro, or methyl; and $R^5$ is hydrogen.

Another aspect of the invention is a compound of Formula I where $R^3$ is triazinyl substituted with 0–1 methyl groups; $R^4$ is hydrogen, chloro, flouro, or methyl; and $R^5$ is hydrogen.

Another aspect of the invention is a compound of Formula I where $R^6$ is hydrogen or methyl Another aspect of the invention is a compound of Formula I where $R^7$ is methyl.

Another aspect of the invention is a compound of Formula I where X—Y—Z is $C(R^7)_2CH_2CH_2$, $C(R^7)_2CH_2CH_2CH_2$, or $C(R^7)_2CH_2CH_2CH_2CH_2$.

Another aspect of the invention is a compound of Formulas

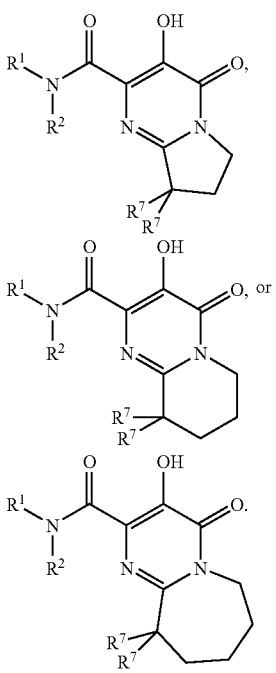

Another aspect of the invention is a compound of Formula I where X—Y—Z is $C(Ar^3)$=$CHCH_2$, $C(Ar^3)$=$CHCH_2CH_2$, or $C(Ar^3)$=$CHCH_2CH_2CH_2$.

Another aspect of the invention is a compound of Formulas

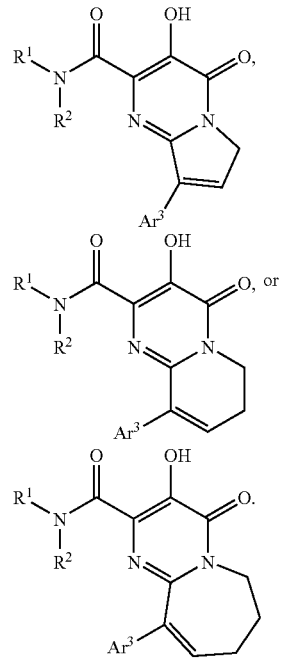

For a compound of Formula I, any scope of $R^1$, $R^2$, $R^3$, $R^4$, $R^5$, $R^6$, $R^7$, $Ar^1$, $Ar^2$, $Ar^3$, and X—Y—Z can be used independently with any scope of any other substituent.

"Alkyl," "alkoxy," "haloalkyl," and related terms with an alkyl moiety include straight and branched configurations. A term such as "$C_{1-6}(R)$alkyl" means a straight or branched alkyl group of one to six carbons substituted with the substituent R. "Haloalkyl" includes all permutations of halogenated alkyl groups, from monohalo to perhalo. "Aryl" means an aromatic ring system and includes carbocyclic and heterocyclic systems. Some substituents are divalent, such as X—Y—Z. Asymmetric divalent substituents may be attached in either of the two configurations.

"Dioxothiazinyl" means

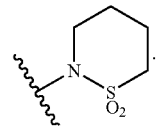

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention also includes all solvated forms of the compounds, particularly hydrates. Solvates do not contribute significantly to the physiological activity or toxicity of the compounds and as such function as pharmacological equivalents. Solvates may form in stoichiometric amounts or may form from adventitious solvent or a combination of both. One type of solvate is hydrate, and some hydrated forms include monohydrate, hemihydrate, and dihydrate.

Some of the compounds of the invention exist in stereoisomeric forms. The invention includes all stereoisomeric forms of the compounds including enantiomers and diastereromers. An example of enantiomers is shown below. Methods of making and separating stereoisomers are known in the art.

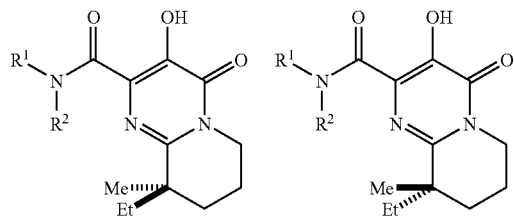

The invention includes all tautomeric forms of the compounds. An example of a tautomeric pair is shown below.

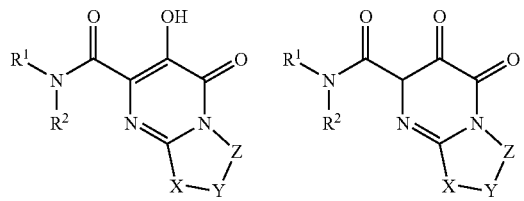

Synthetic Methods

The compounds of this invention can be made by various methods known in the art including those of the following schemes and in the specific embodiments section. The variables shown in the synthetic schemes are distinct from and should not be confused with the variables in the claims or the rest of the specification. The variables in the schemes are meant only to illustrate how to make some of the compounds of this invention.

Some compounds can be synthesized from an appropriately substituted heterocycle I-1 according to Scheme I, where $R_a$ and P can serve as protecting groups (see Greene, T. W. and Wutz, P. G. M. Protective Groups in Organic Synthesis, Second Edition, 1991, John Wiley and Sons, New York). When P is benzyl or substituted benzyl it can be removed by hydrogenolysis ($H_2$—Pd/C) or acid hydrolysis (trifluoroacetic acid) to yield intermediate I-2. I-2 can be transaminated to I-4 by reaction with amine I-3. In a number of cases this reaction can be carried out by heating I-3 and I-2 together in the presence of base. Alternatively, standard amide coupling reagents can be used to effect the formation of the amide bond. When $R_a$ is a lower alkyl group, $R_a$ can be removed under ester hydrolysis conditions, such as treatment with NaOH, LiOH, or KOH to deliver the corresponding carboxylic acid I-5. Alternatively, $R_a$ can be removed by nucleophilic displacement using NaI. When $R_a$ is benzyl and substituted benzyl, $R_a$ can be removed by hydrogenolysis. Intermediate I-5 can be coupled using amide bond forming reagents such as BOP, DCC, EDCI, PyBrop, PyBop or other reagents (see March, J. Advanced Organic Chemistry, Fourth Edition 1992 John Wiley & Sons, New York). The resulting intermediate I-6 can be deprotected as described for intermediate I-1.

Scheme I.

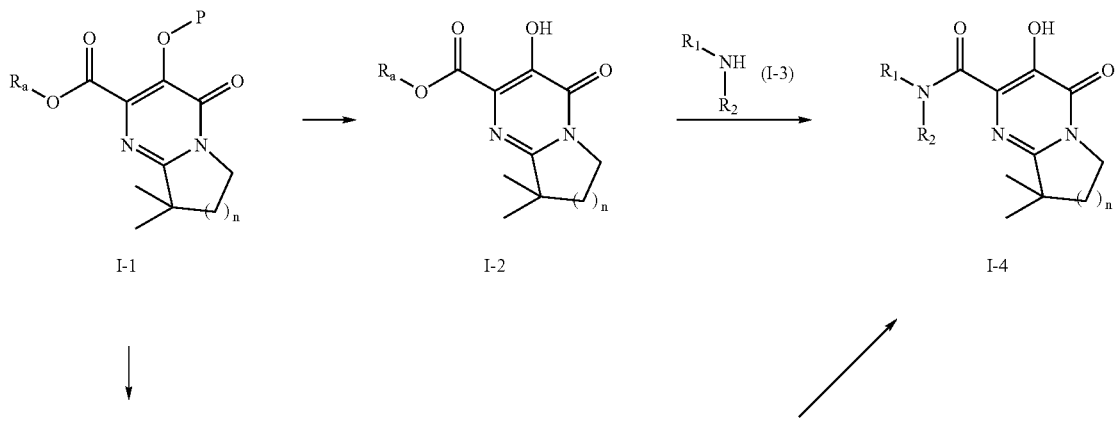

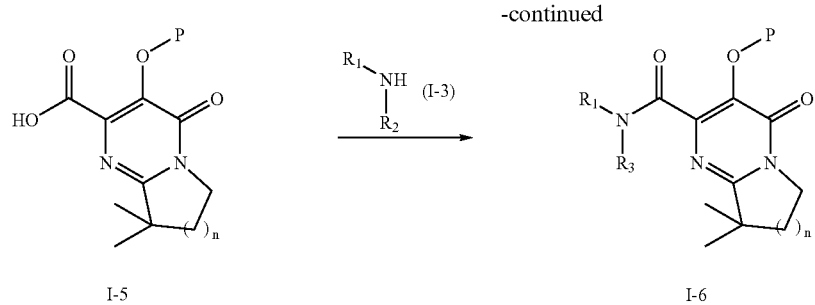

I-5 → I-6

(P = protecting group)
$R_a$ = alkyl, aryl, benzyl

In Scheme II, intermediate II-3 can be prepared using methods similar to those described in Sunderland, J. S.; Botta, M.; Aime, S.; Raymond, K. N. Inorg. Chem. (2001), 40, 6756–6756, where II-1 and II-2 are condensed, to provide intermediate II-3. This reaction is usually conducted in the presence of a base such as sodium hydride (NaH), sodium ethoxide (EtONa) or lithium hexamethyldisilazide (LiHMDS). Using the methods described in the reference, II-3 can be condensed with an appropriately substituted amidine II-4 to form II-5. Substituent B can be a leaving group, such as—halo (Cl, Br or I) or can be converted to a leaving group under appropriate conditions such as by forming the corresponding methylsulfonate ester. When substituent B is a methyl sulphide group it can be treated with iodomethane to form a dimethylsulfonium intermediate which is activated towards nucleophilic attack to effect ring closure.

Scheme II

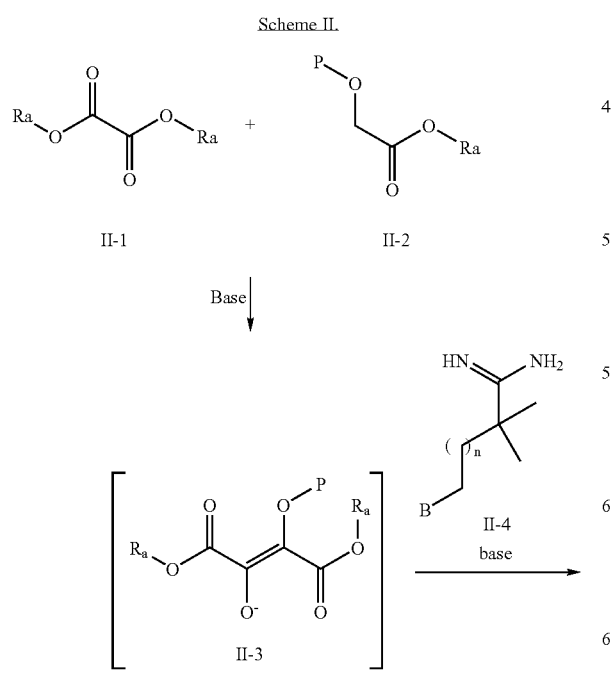

In Scheme III, intermediate II-3 can be condensed with a cyclic-amidine to yield intermediate I-1. Intermediate III-1 can be prepared using known methods (see Patai, S. and Rappoport, Z. The Chemistry of Amidines and Imidates, Volume 2, 1991, John Wiley & Sons, New York).

Scheme III

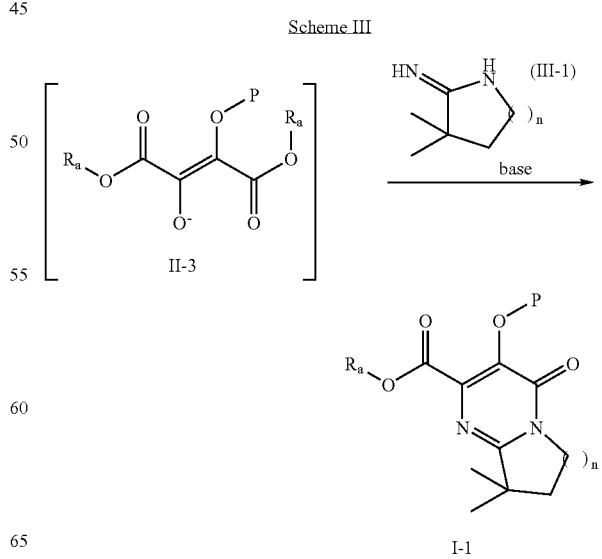

In Scheme IV, nitrile IV-1, possessing a potential leaving group B, can be reacted with hydroxylamine to form intermediate IV-2. This intermediate can be reacted with a suitably protected alkyne to form IV-3 which can rearrange to from intermediate IV-4 according to literature methods (Culbertson, T. P. *Journal of Heterocyclic Chemistry*, 1979, 16, 1423–1424).

Scheme IV.

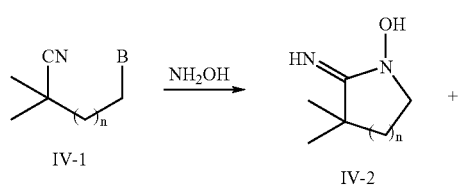

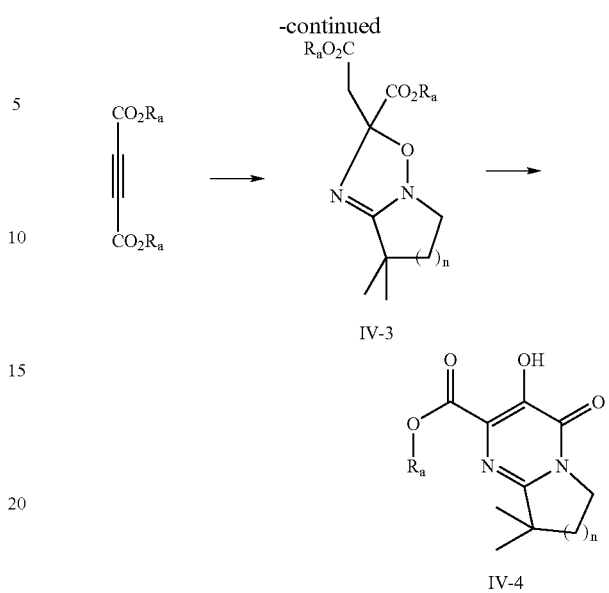

Schemes V–VIII provide further illustrations of the synthesis of the compounds of the current invention.

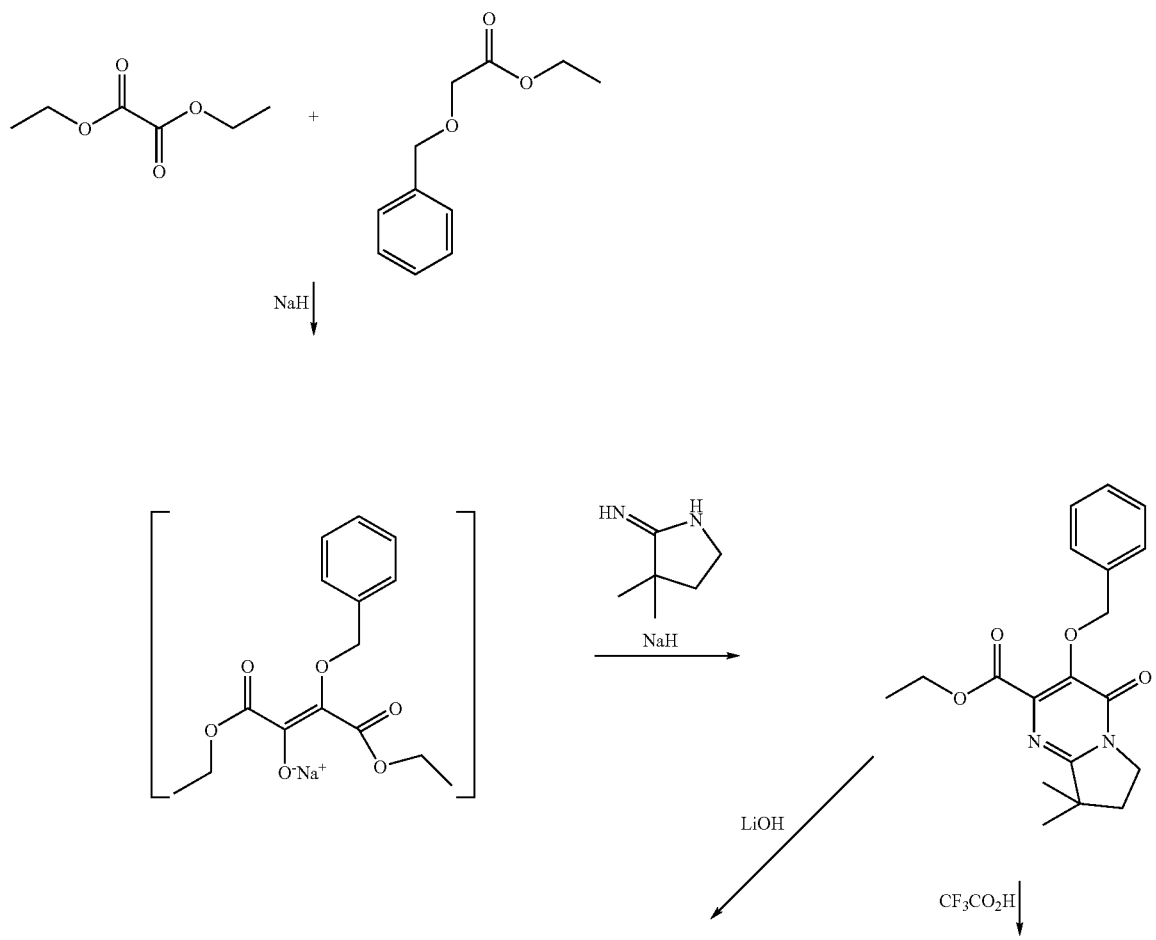

11 12
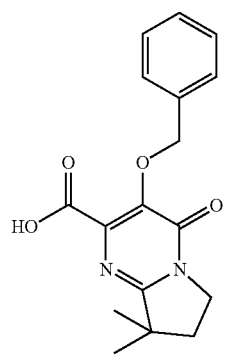
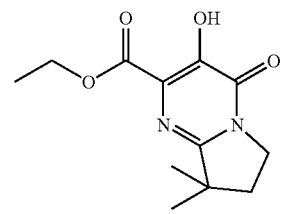
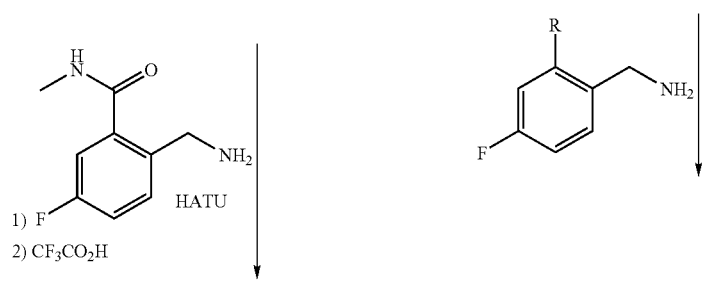
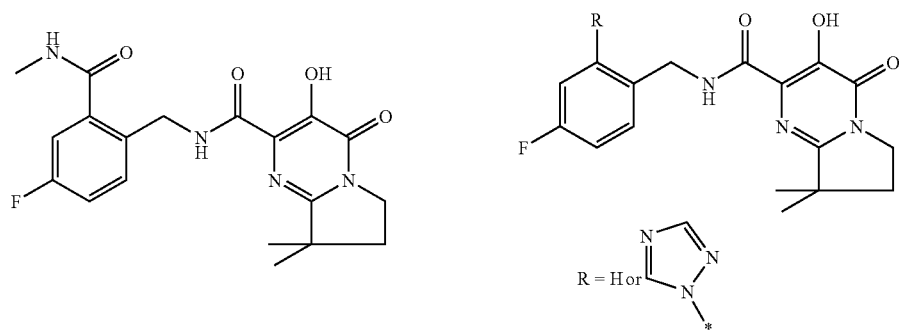
R = H or
Scheme VI
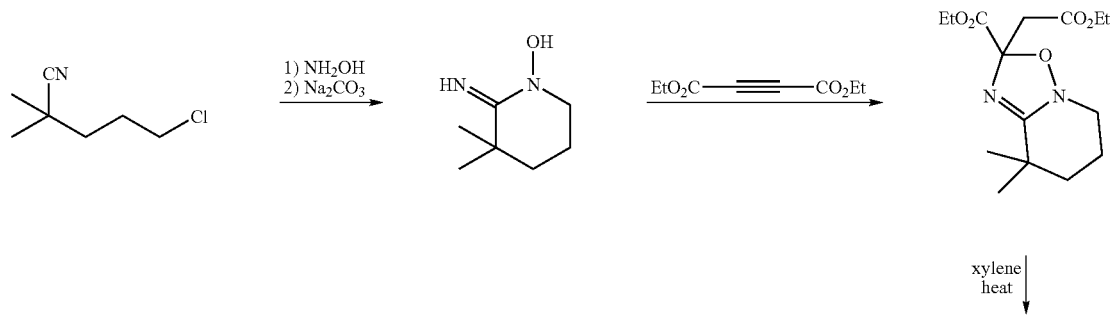
xylene heat -continued
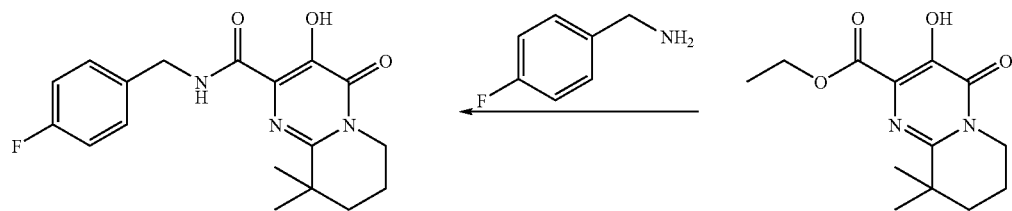
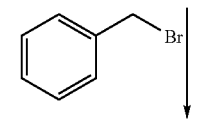
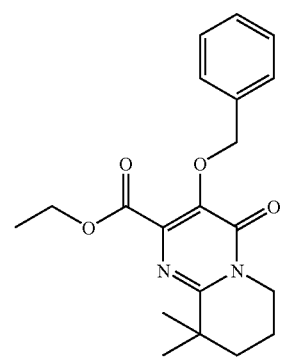
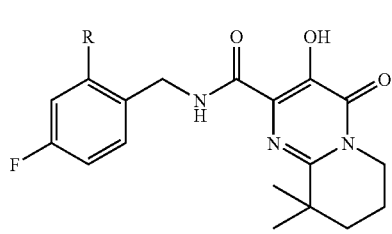
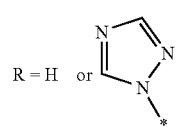

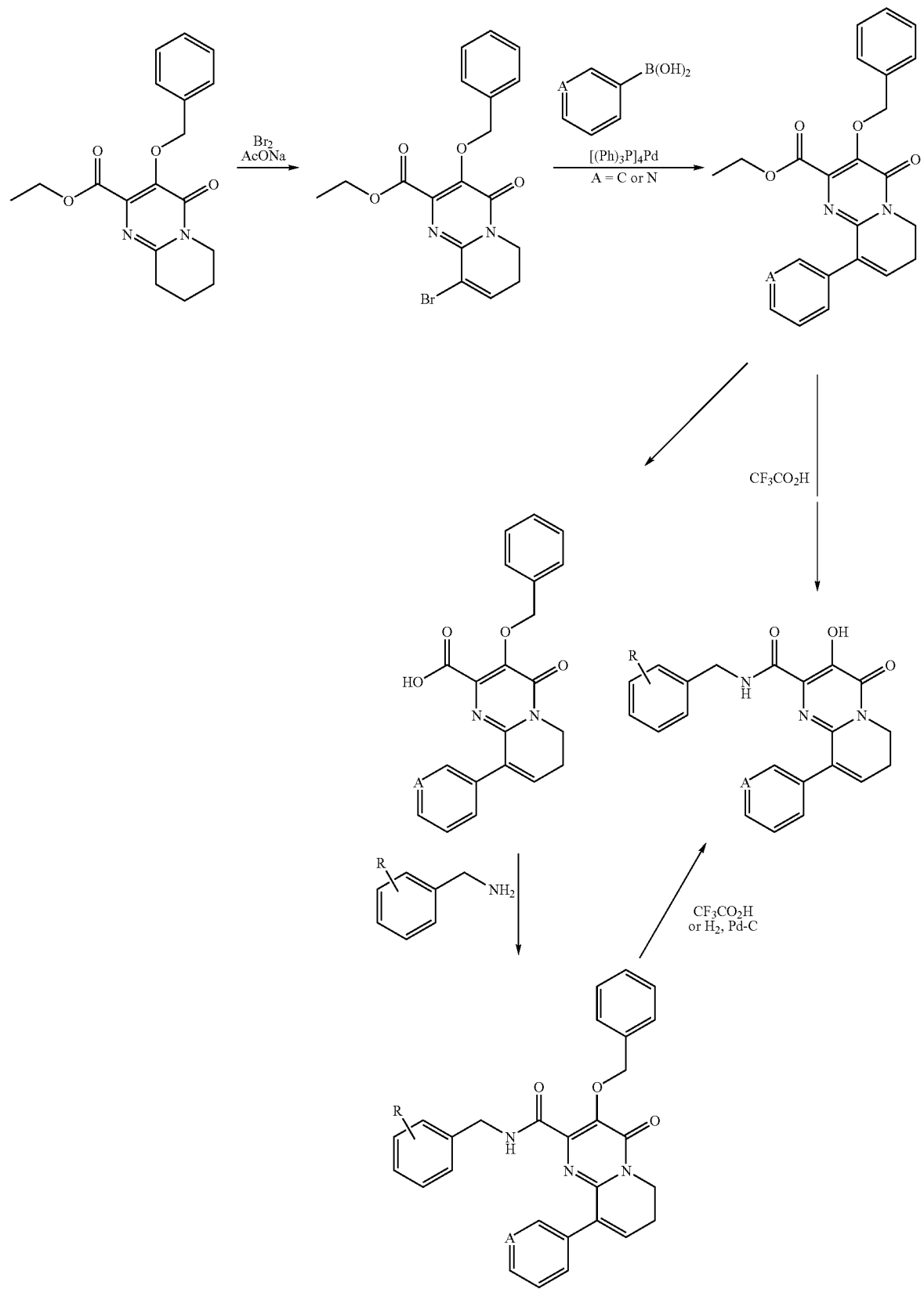

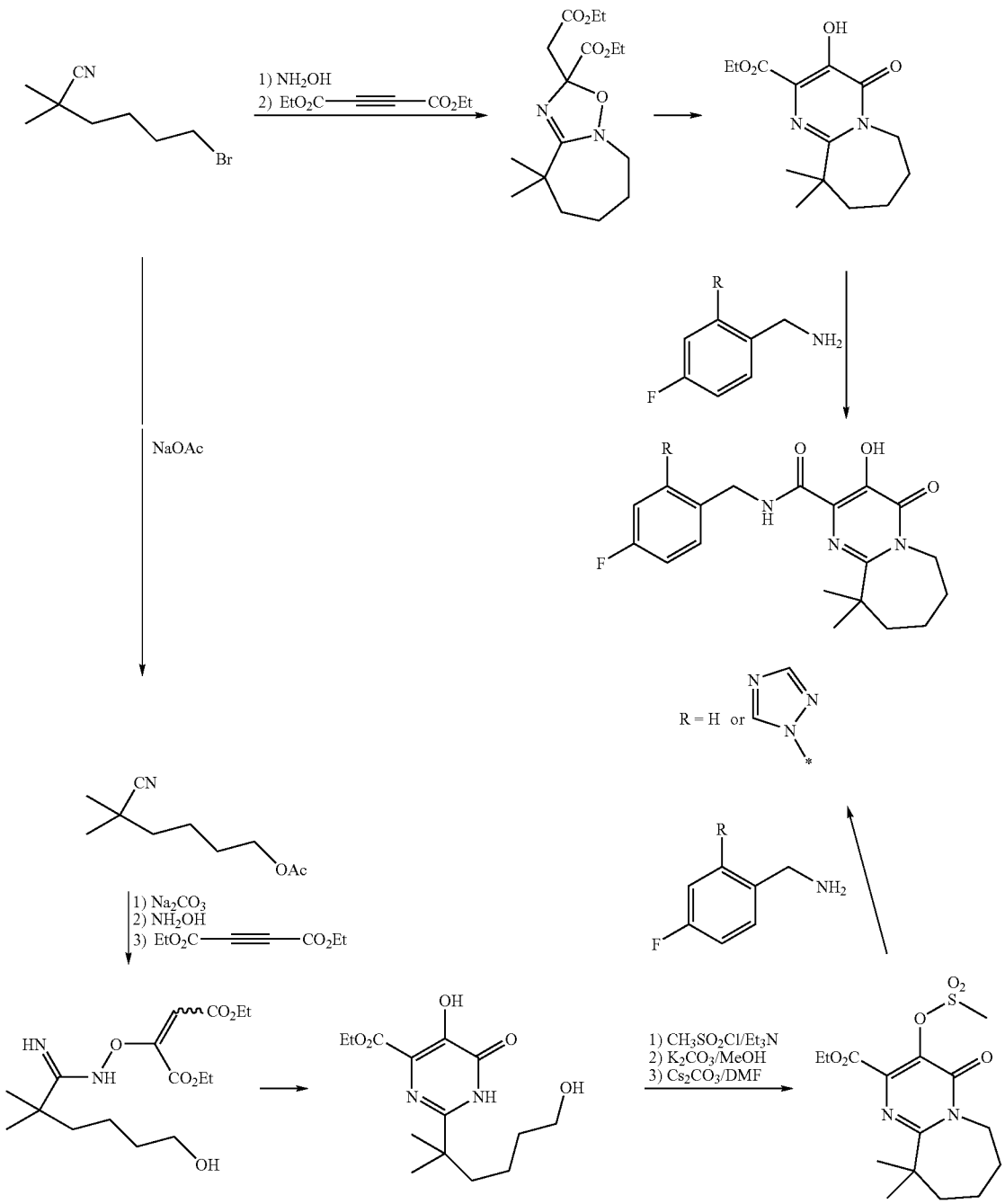

Scheme VIII

Biological Methods

Another aspect of the invention is a method for inhibiting HIV integrase comprising contacting a compound of Formula I with HIV integrase.

Another aspect of the invention is a method for inhibiting HIV viral DNA integration into human DNA comprising administering an effective amount of a compound of Formula I to a human cell infected with HIV.

HIV-Integrase InhibitionActivity. To evaluate in-vitro activity against HIV-integrase, 5 pmole of biotin labeled substrate DNA was bound to 100 μg of Streptavidin coated PVT SPA beads (Amersham Pharmacia Biotech). Recombinant integrase (0.26 ng) was incubated with the beads for 90 min at 37° C. Unbound enzyme was removed by washing the complex followed by addition of inhibitors and 0.1 fmol of P33 labeled target DNA. The reaction was stopped by adding EDTA to a final concentration of 10 mM. Samples were counted in TopCountNXT (Packard) and the CPM was used as a measure of integration. The reaction condition was as described in A. Engelman and R. Craigie, *J. Virol* 69, 5908–5911 (1995). The sequences of substrate and target DNA were described in *Nucleic Acid Research* 22, 1121–1122 (1994). Results are shown in Table 1. Activity equal to A refers to a compound having $IC_{50}$=0.002 to 0.009 μM while B and C denote compounds having $IC_{50}$=0.010 to 049 μM and $IC_{50} \geq 0.05$ μM respectively.

TABLE 1

| Example | Activity |
|---------|----------|
| 1 | A |
| 2 | B |
| 3 | A |
| 4 | A |
| 5 | A |
| 6 | A |
| 7 | A |
| 8 | A |
| 9 | A |
| 10 | A |
| 11 | A |
| 12 | A |
| 13 | A |

Inhibition of HIV replication. A recombinant NL-Rluc virus was constructed in which a section of the nef gene from NL4-3 was replaced with the Renilla Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv on 293T cells using the LipofectAMINE PLUS kit from Invitrogen (Carlsbad, Calif.) according to manufactures instruction, and the pseudotype virus generated was titered in MT-2 cells.

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71–76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in Table 2. Activity equal to A refers to a compound having $EC_{50}$=0.001 to 0.009 μM while B and C denote compounds with $EC_{50}$=0.01 to 0.02 μM and $EC_{50} \geq 0.021$ μM respectively.

TABLE 2

| Example | Activity |
|---------|----------|
| 1 | B |
| 2 | A |
| 3 | A |
| 4 | A |
| 5 | A |
| 6 | A |
| 7 | A |
| 8 | B |
| 9 | A |
| 10 | C |
| 11 | C |
| 12 | A |
| 13 | A |

Pharmaceutical Composition and Methods of Use

The compounds of this invention inhibit HIV integrase. HIV integrase inhibitors belonging to a class of diketo acid compounds prevented viral integration and inhibited HIV-1 replication in cells (Hazuda et al. *Science* 2000, 287, 646). Recently, HIV integrase inhibitors have been accepted into clinical trials for treating AIDS and HIV infection (Neamati *Expert. Opin. Ther. Patents* 2002, 12, 709, Pais and Burke *Drugs Fut.* 2002, 27, 1101).

Accordingly, another aspect of the invention is a method for treating HIV infection in a human patient comprising administering a therapeutically effective amount of a compound of Formula I, or a pharmaceutically acceptable salt or solvate thereof, with a pharmaceutically acceptable carrier.

Another aspect of the invention is a method for treating HIV infection in a human patient comprising administering a therapeutically effective amount of a compound of Formula I, or a pharmaceutically acceptable salt or solvate thereof, with a therapeutically effective amount of at least one other agent used for treatment of AIDS or HIV infection. Some suitable agents are nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a composition for treating HIV infection in a human patient comprising administering a therapeutically effective amount of a compound of Formula I, or a pharmaceutically acceptable salt or solvate thereof, with a pharmaceutically acceptable carrier.

"Combination," "coadministration," "concurrent," and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25–1000 mg/unit.

Liquid compositions are usually in dosage unit ranges. Generally, the liquid composition will be in a unit dosage range of 1–100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1–100 mg/mL.

The invention encompasses all conventional modes of administration; oral and parenteral methods are preferred. Generally, the dosing regimen will be similar to other antiretroviral agents used clinically. Typically, the daily dose will be 1–100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1–100 mg/kg body weight daily in conjunction with other agents. The other agents generally will be given in the amounts used therapeutically. The specific dosing regime, however, will be determined by a physician using sound medical judgement.

Table 3 lists some agents useful in treating AIDS and HIV infection which are suitable for this invention.

TABLE 3

| DRUG NAME | MANUFACTURER | INDICATION |
|---|---|---|
| ANTIVIRALS | | |
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection, ARC, PGL HIV positive, AIDS |
| Alpha Interferon | Glaxo Wellcome | Kaposi's sarcoma |
| HIV in combination w/Retrovir | | |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/Novartis | HIV infection, AIDS, ARC |
| BMS-234475 (CGP-61755) (protease inhibitor) | Bristol-Myers Squibb/Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combinationwith AZT/d4T |
| DMP-450 (protease inhibitor) | AVID (Camden, NJ) | HIV infection, AIDS, ARC |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |
| EL10 | Elan Corp, PLC (Gainesville, GA) | HIV infection |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside reverse transcriptaseinhibitor) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |

TABLE 3-continued

| DRUG NAME | MANUFACTURER | INDICATION |
|---|---|---|
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine (RT inhibitor) | Boeheringer Ingleheim | HIV infection, AIDS, ARC |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxythymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (reverse transcriptase inhibitor) | Gilead | HIV infection, AIDS |
| Combivir ® (reverse transcriptase inhibitor) | GSK | HIV infection, AIDS |
| abacavir succinate (or Ziagen ®) (reverse transcriptase inhibitor) | GSK | HIV infection, AIDS |
| Reyataz ® (atazanavir) | Bristol-Myers Squibb | HIV infection, AIDS |
| Fuzeon (Enfuvirtide, T-20) | Roche/Trimeris | HIV infection, AIDS, viral fusion inhibitor |
| Trizivir ® | | HIV infection, AIDS |
| Kaletra ® | Abbott | HIV infection, AIDS, ARC |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246, 738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/ TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide Granulocyte Colony Stimulating Factor | Ciba-Geigy Corp. Amgen | Kaposi's sarcoma AIDS, in combination w/AZT |
| Remune | Immune Response Corp. | Immuno-therapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |

TABLE 3-continued

| DRUG NAME | MANUFACTURER | INDICATION |
|---|---|---|
| Interferon Alfa 2a | Hoffman-La Roche in combination w/AZT | Kaposi's sarcoma, AIDS, ARC |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

DESCRIPTION OF SPECIFIC EMBODIMENTS

Method A. General procedure for amide bond formation. A mixture of intermediate ester (0.15 mmol) and benzylamine (0.87 mmol) in anhydrous ethyl alcohol (5 ml) and N,N-dimethylformamide (2 ml) are heated under reflux for 18 h. The solvent is then evaporated in vacuo and the remaining residue partitioned between ethyl acetate and 0.1 N hydrochloric acid. The organic phase is washed with water and brine then dried over anhydrous sodium sulfate. Evaporation of the solvent provides the crude product which can be purified by recrystallization from ethanol or methanol.

Method B. General procedure for amide bond formation. A mixture of intermediate carboxylic acid (0.54 mmol) and benzylamine (0.60 mmol) in dichloromethane (10 ml) is treated at 22° C. with triethylamine (0.17 ml, 1.22 mmol) followed by benzotriazole-1-yloxy-tris-pyrrolidino-phosphonium hexafluorophosphate (PyBOP) (0.340 g, 0.65 mmol). After 3 h, the reaction mixture is diluted with ethyl acetate, washed with saturated sodium bicarbonate and brine, then dried over anhydrous magnesium sulfate. Evaporation of the solvent followed by chromatography of the residue on silica gel provides the pure product.

Method C. General procedure for hydrogenolysis of the benzyl group. A solution of benzylated intermediate (0.56 mmol) in a mixture of ethyl acetate (25 ml) and ethanol (25 ml) is hydrogenated under 1 atm of hydrogen at 25° C. over 10% palladium on activated carbon (0.09 g) for 2.5 h. The reaction mixture is filtered through Celite and the solvent removed provide the product.

Method D. General procedure for acid mediated hydrolysis of the benzyl group. A solution of benzylated intermediate (0.32 mmol) in trifluoroacetic acid (2 mL) is stirred at room temperature for 2.5 hrs, after which the mixture is concentrated in vacuo to dryness. The residual oil can be crystallized from 95% ethanol to provide pure product.

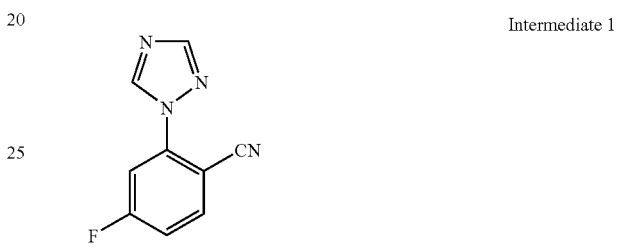

Intermediate 1

4-Fluoro-2-(1H-1,2,4-triazol-1-yl)benzonitrile. To a solution of 2,4-difluorobenzonitrile (10 g, 72 mmol), dissolved in THF (20 mL) and DMF (40 mL), was added 1,2,4-triazole sodium salt (6.3 g, 70 mmol) and the resulting mixture stirred at 90° C. for 3 h, after which it was filtered and concentrated. The remaining residue was adsorbed onto silica gel and purified by flash column chromatography eluting with 0%–30% ethyl acetate/hexanes to give the title compound as colorless needles (2.46 g, 18% yield). $^1$H NMR (500 MHz, CDCl$_3$) δ ppm: 8.89 (1H, s), 8.19 (1H, s), 7.85 (1H, dd, J=8.7, 5.6 Hz), 7.60 (1H, dd, J=8.8, 2.4 Hz), 7.28–7.24 (1H, m). LCMS (M+H) calcd for C$_9$H$_6$N$_4$F: 189.05; found: 189.13.

Intermediate 2

(4-Fluoro-2-(1H-1,2,4-triazol-1-yl)phenyl)methanamine hydrochloride): Intermediate 1,4-fluoro-2-(1H-1,2,4-triazol-1-yl)benzonitrile, (2.46 g, 13.13 mmol) was dissolved in hot ethanol (150 mL). Aqueous 1N HCl (15 mL) was added followed by 10% Pd/C (200 mg). The mixture was shaken under H$_2$ (55 psi) for 4 h., then filtered through Celite and concentrated in vacuo. The remaining residue was partitioned between ethyl acetate and water. The aqueous layer was isolated and lyophilized to give the title compound as a white powder (2.96 g, 99% yield). $^1$H NMR (500 MHz, CD$_3$OD) δ ppm: 9.51 (1H, s), 8.63 (1H, s), 7.85 (1H, dd, J=8.5, 5.8 Hz), 7.68 (1H, dd, J=8.8, 2.4 Hz), 7.49 (1H, td, J=8.3, 2.4 Hz), 4.20 (2H, s). LCMS (M+H) calcd for $C_9H_{10}N_4F$: 193.08; found: 193.16.

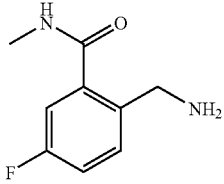

Intermediate 3

2-Aminomethyl-5-fluoro-N-methyl-benzamide trifluoroacetic acid salt. To a solution of tert-butyl 4-fluoro-2-(methylcarbamoyl)benzylcarbamate (7.70 g, 27.3 mmol; prepared from 2-bromo-5-fluorobenzoic acid using literature methods) in $CH_2Cl_2$ (100 mL) was added $CF_3CO_2H$ (25 mL) and the mixture stirred at room temperature for 15 min. This was concentrated in vacuo and the residue triturated with diethyl ether to provide 8.0 g (Yield 99%) of the title compound as a white powder. $^1$H NMR (300 MHz, $D_2O$) δ ppm: 2.93 (3H, s) 4.20 (2H, s) 7.35 (1H, dt, J=8.5, 3 Hz) 7.42 (1H, dd, J=9.0, 2.7 Hz) 7.57 (1H, dd, J=8.4, 5.5 Hz); LC/MS m/z 183 (M+H).

EXAMPLES 1–3

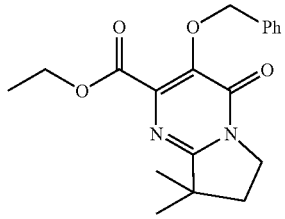

Intermediate 4

Ethyl 3-(benzyloxy)-8,8-dimethyl-4-oxo-4, 6,7,8-tetrahydropyrrolo[1,2-a]pyrimidine-2-carboxylate. A stirred solution of ethyl benzyloxyacetate (3.88 g, 0.02 mol) and diethyl oxalate (2.92 g, 0.02 mol) in 30 mL tetrahydrofuran was treated portion-wise with 60% NaH (800 mg, 0.02 mol) under $N_2$ at room temperature. A few drops of ethanol were added and stirring continued for 7 days, after which the mixture was concentrated in vacuo. The remaining residue was dissolved in 30 mL ethanol and to it was added a solution of 3,3-dimethylpyrrolidin-2-imine (1.12 g, 0.01 mol, prepared using a literature method). The mixture was treated with NaH (400 mg, 0.01 mol; 60% oil dispersion) and triethylamine (2 grams) then stirred for 16 hrs. The solvent was removed in vacuo and the remaining residue dissolved in $CH_2Cl_2$ and washed with $H_2O$. The organic layer was dried and concentrated to give a dark oil. This was purified by chromatography on silica gel eluting with 9:1 $CH_2Cl_2$:ether to provide 1.3 grams of the title compound as a colorless oil which crystallized on standing (Yield=38%). $^1$H NMR (300 MHz, $CDCl_3$) δ ppm:7.39–7.48 (2 H, m) 7.25–7.37 (3 H, m) 5.21 (2 H, s) 4.30 (2 H, q, J=7.3 Hz) 3.99–4.11 (2 H, m) 2.03–2.15 (2 H, m) 1.34 (6 H, s) 1.26 (3 H, t, J=7.1 Hz); LC/MS m/z 343 (M+H).

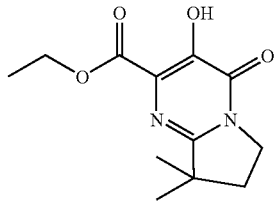

Intermediate 5

Ethyl 3-hydroxy-8,8-dimethyl-4-oxo-4,6,7,8-tetrahydropyrrolo[1,2-a]pyrimidine-2-carboxylate. Intermediate 4, ethyl 3-(benzyloxy)-8,8-dimethyl-4-oxo-4,6,7,8-tetrahydropyrrolo[1,2-a]pyrimidine-2-carboxylate, (650 mg, 1.9 mmol) was treated with 6 mL trifluoroacetic acid (16 hrs) then concentrated in vacuo. The remaining residue was dissolved in $CH_2Cl_2$ and washed with $H_2O$. Concentration of the $CH_2Cl_2$ layer gave 430 mg of a solid (Yield=90%) which could be further purified by trituration with diethyl ether. $^1$H NMR (300 MHz, $CDCl_3$) δ ppm: 10.81 (1 H, s) 4.45 (2 H, q, J=7.0 Hz) 3.97–4.12(2 H, m) 1.95–2.15 (2 H, m) 1.41 (3 H, t, J=7.1 Hz) 1.33 (6 H, s); LC/MS m/z 253 (M+H).

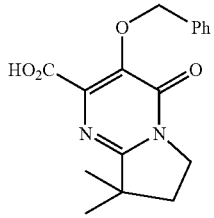

Intermediate 6

3-(Benzyloxy)-8,8-dimethyl-4-oxo-4,6,7,8-tetrahydropyrrolo[1,2-a]pyrimidine-2-carboxylic acid. Intermediate 4, ethyl 3-(benzyloxy)-8,8-dimethyl-4-oxo-4,6,7,8-tetrahydropyrrolo[1,2-a]pyrimidine-2-carboxylate (342 mg, 1 mmol) was suspended in 5 mL of methanol, treated with a solution of LiOH (48 mg, 2 mmol) in 5 ml $H_2O$ then stirred at room temperature for 1 h. The reaction was quenched with 2 mL of 1N HCl. The resulting precipitate was collected by filtration and dried to give 260 mg of the title compound as a crystalline solid (Yield=83%). $^1$H NMR (300 MHz, $CDCl_3$) δ ppm: 7.46–7.59 (2 H, m) 7.25–7.40 (3 H, m) 5.44 (2 H, s) 3.98–4.15 (2 H, m) 2.04–2.19 (2 H, m) 1.34 (6 H, s); LC/MS m/z 315 (M+H).

EXAMPLE 1

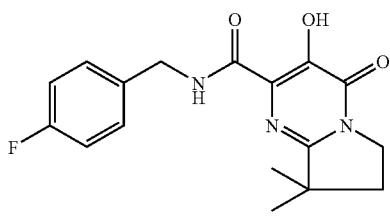

N-(4-Fluorobenzyl)-3-hydroxy-8,8-dimethyl-4-oxo-4,6,7,8-tetrahydropyrrolo[1,2-a]pyrimidine-2-carboxamide. The title compound was prepared from intermediate 5 and 4-fluorobenzyl amine using Method A. ¹H NMR (300 MHz, CDCl₃) δ ppm: 12.12 (1H, s), 7.93 (1H, br), 7.26–7.33 (2H, m), 6.98–7.07 (2H, m), 4.56 (2H, d, J=6.2 Hz), 4.00–4.08 (2H, m), 2.00–2.09 (2H, m), 1.28 (6H, s); HRMS (ESI) calcd for $C_{17}H_{19}FN_3O_3$ (M+H) 332.1410, found 332.1394.

Intermediate 7

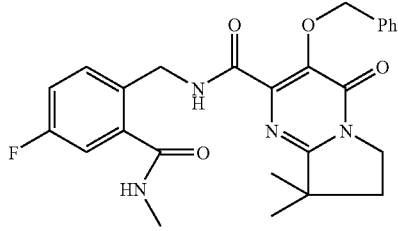

N-(4-Fluoro-2-(methylcarbamoyl)benzyl)-3-(benzyloxy)-8,8-dimethyl-4-oxo-4,6,7,8-tetrahydropyrrolo[1,2-a]pyrimidine-2-carboxamide. Intermediate 6, 3-(benzyloxy)-8,8-dimethyl-4-oxo-4,6,7,8-tetrahydropyrrolo[1,2-a]pyrimidine-2-carboxylic acid, (79 mg, 0.25 mmol) was placed together with O-(7-azobenzotriazol-1-yl)-1,1,3,3-tetramethyluronium hexafluorophosphate, HATU, (114 mg, 0.3 mmol) in 2 mL DMF under $N_2$ and stirred for 20 min. 4-(Dimethylamino)pyridine, DMAP, (100 mg, 0.8 mmol) and intermediate 3, 2-aminomethyl-5-fluoro-N-methylbenzamide trifluoroacetic acid salt (89 mg, 0.3 mmol) in 1 mL DMF were added and stirring continued for 20 min. The reaction mixture was concentrated, the residue dissolved in $CH_2Cl_2$ and washed with $H_2O$. The $CH_2Cl_2$ layer was separated, dried ($MgSO_4$), filtered and concentrated to give 118 mg of a the title compound as a solid (Yield=95%). ¹H NMR (300 MHz, CDCl₃) δ ppm: 8.31–8.46 (1 H, m) 7.24–7.46 (5 H, m) 6.95–7.15 (3 H, m) 6.88 (1 H, s) 5.23 (2 H, s) 4.48 (2 H, d, J=6.6 Hz) 3.95–4.10 (2 H, m) 2.93 (3 H, t, J=5.1 Hz) 2.00–2.16 (2 H, m) 1.34 (6 H, s); LC/MS m/z 479 (M+H).

EXAMPLE 2

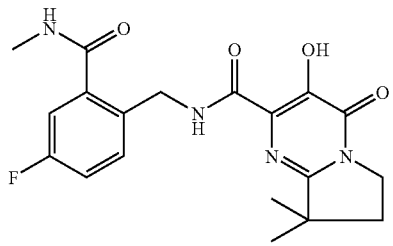

N-(4-Fluoro-2-(methylcarbamoyl)benzyl)-3-hydroxy-8,8-dimethyl-4-oxo-4,6,7,8-tetrahydropyrrolo[1,2-a]pyrimidine-2-carboxamide. Intermediate 7, N-(4-fluoro-2-(methylcarbamoyl)benzyl)-3-(benzyloxy)-8,8-dimethyl-4-oxo-4,6,7,8-tetrahydropyrrolo[1,2-a]pyrimidine-2-carboxamide was treated with trifluoroacetic acid, according to Method D to provide the title compound ¹H NMR (300 MHz, CDCl₃) δ ppm: 12.12 (1H, br), 8.71 (1H, br), 7.47 (1H, dd, J=8.1, 5.5 Hz), 7.05–7.2 (2H, m), 6.26 (1H, br), 4.59 (2H, d, J=6.6 Hz), 3.95–4.06 (2H, m), 3.00 (3H, d, J=4.8 Hz), 1.99–2.08 (2H, m), 1.31 (6H, s); HRMS (ESI) calcd for $C_{19}H_{22}FN_4O_4$(M+H) 389.1625, found 389.1625.

EXAMPLE 3

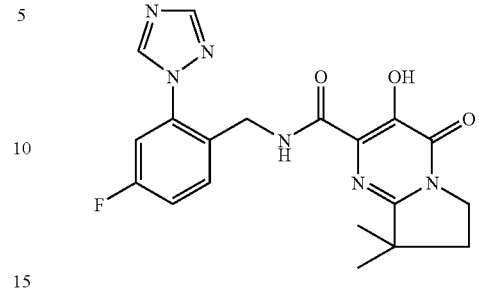

N-(4-fluoro-2-(1H-1,2,4-triazol-1-yl)benzyl)-3-hydroxy-8,8-dimethyl-4-oxo-4,6,7,8-tetrahydropyrrolo[1,2-a]pyrimidine-2-carboxamide. The title compound was prepared from intermediate 5 and intermediate 2 using Method A. ¹H NMR (300 MHz, CDCl₃) δ ppm: 12.02 (1H, s), 8.70 (1H, t, J=6.2 Hz), 8.41 (1H, s), 8.18 (1H, s), 7.65 (1H, dd, J=8.8, 5.9 Hz), 7.18 (1H, dt, J=8.1, 2.7 Hz), 7.08 (1H, dd, J=8.4, 2.6 Hz), 4.47 (2H, d, J=6.6 Hz), 3.97–4.09 (2H, m), 2.01–2.09 (2H, m), 1.30 (6H, s); HRMS (ESI) calcd for $C_{19}H_{20}FN_6O_6$ (M+H) 399.1581, found 399.1599.

EXAMPLES 4–6

Intermediate 8

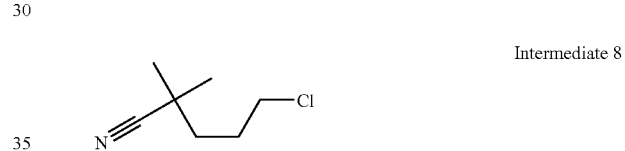

5-Chloro-2,2-dimethylpentanenitrile. To a solution of isobutyronitrile (13.8 g, 0.2 mol; Aldrich) in hexanes (200 mL) was added a 2M solution of lithium diisopropylamide (100 mL, 0.2 mol; Aldrich), and the mixture stirred for 2 hrs under nitrogen. This mixture was added to a solution of 1-bromo-3-chloropropane (34.6 g, 0.22 mol; Aldrich) and stirred for 1 h. The reaction was quenched by careful addition of water, and the hexane layer was dried ($Na_2SO_4$), filtered, and concentrated. The residue was purified by column chromatography ($SiO_2$, 20–50% $CH_2Cl_2$ in Hexanes) to provide 10 g (68.7 mmol, Yield=34%) of the title compound as an amber oil: ¹H NMR (CDCl₃, 500 MHz) δ ppm: 1.35 (6H, s, gem-Me), 1.67 (2H, m, $CH_2$), 1.95 (2H, m, $CH_2$), 3.57 (2H, t, J=6.5 Hz, Cl-$CH_2$); ¹³C NMR (CDCl₃, 125.8 Hz) δ ppm 26.73, 28.50, 32.08, 38.47, 44.58, 124.72.

Intermediate 9

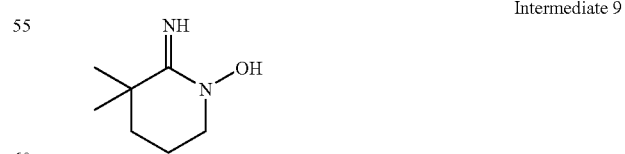

2-Imino-3,3-dimethyl-piperidin-1-ol. A solution of intermediate 8, 5-chloro-2,2-dimethylpentanenitrile, (725 mg, 5.0 mmol) and 50% aqueous $NH_2OH$ (1.0 g, 15 mmol; Aldrich) in ethanol (1.5 mL) was stirred at room temperature for 5 days, and then treated with $Na_2CO_3$ (265 mg, 2.5 mmol). The mixture was stirred at room temperature for 1 h, and concentrated in vacuo to provide 1.0 g of the title compound as crude brown oily solid. $^1$H NMR (DMSO-d6, 500 MHz) δ ppm: 1.29 (6H, s, Me), 1.59 (2H, m, CH$_2$), 1.85 (2H, m, CH$_2$), 3.62 (2H, t, J=6 Hz, NCH$_2$); $^{13}$C NMR (CDCl$_3$, 125.8 Hz) δ ppm: 18.23, 26.63, 33.57, 35.09, 51.85, 162.76.

Intermediate 10

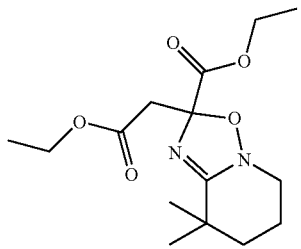

2-Ethoxycarbonylmethyl-8,8-dimethyl-5,6,7,8-tetrahydro-2H-[1,2,4]oxadiazolo[2,3-a]pyridine-2-carboxylic acid ethyl ester. To a solution intermediate 9,2-imino-3,3-dimethyl-piperidin-1-ol (1.0 g) in ethanol (5 mL) and water (5 mL) was added diethyl acetylene dicarboxylate (935 mg, 5.5 mmol; Avocado organics), and the mixture stirred at room temperature for 40 min. The mixture was extracted with ethylcacetate (20 mL) and the extract washed with brine, dried (Na$_2$SO$_4$), filtered, and concentrated in vacuo. The dark oily residue was purified by column chromatography (SiO$_2$, 10% ethyl acetate in CH$_2$Cl$_2$) to provide 816 mg (Yield 52% over 2 steps) of title compound as a clear oil: $^1$H NMR (CDCl$_3$, 500 MHz) δ ppm: 1.17 (3H, t, J=7 Hz, Me), 1.19 (3H, s, Me), 1.20 (3H, s, Me), 1.22 (3H, t, J=7 Hz, Me), 1.49 (2H, t, J=6 Hz, CH$_2$), 1.88 (2H, m, CH$_2$), 2.79–2.85–3.22–3.27 (2H, ABq, CH$_2$), 3.26–3.43 (2H, m, NCH$_2$), 4.06 (2H, q, J=7 Hz, OCH$_2$), 4.1–4.3 (2H, m, OCH$_2$); $^{13}$C NMR (CDCl$_3$, 125.8 Hz) δ ppm: 13.86, 13.98, 20.29, 26.73, 26.76, 35.47, 37.25, 42.11, 56.07, 60.50, 61.74, 103.27, 168.39, 168.65, 171.82. HRMS (ESI) calcd for C$_{15}$H$_{25}$N$_2$O$_5$ (M+H) 313.1763, found 313.1754.

Intermediate 11

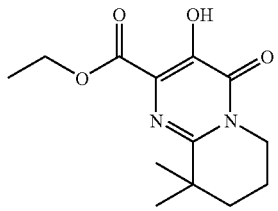

3-Hydroxy-9,9-dimethyl-4-oxo-6,7,8,9-tetrahydro-4H-pyrido[1,2-a]pyrimidine-2-carboxylic acid ethyl ester. A solution of intermediate 10, 2-ethoxycarbonylmethyl-8,8-dimethyl-5,6,7,8-tetrahydro-2H-[1,2,4]oxadiazolo[2,3-a]pyridine-2-carboxylic acid ethyl ester, (600 mg, 1.92 mmol) in 1,2,4-trimethylbenzene (30 mL) was stirred in an oil bath heated at 180° C. for 20 hrs. The solvent was evaporated in vacuo, and the oily residue dissolved in ethyl acetate (20 mL) was stirred with 1M aqueous sodium carbonate (5 mL). The resulting precipitate was filtered, washed with water and ether, then dried in vacuo to provide 213 mg (0.74 mmol, Yield=39%) of the title compound as a yellow powder. A portion of the sodium salt was also converted to the free acid form: $^1$H NMR (CDCl$_3$, 500 MHz) δ ppm: 1.34 (6H, s, gem-Me), 1.38 (3H, t, J=7 Hz, Me), 1.72 (2H, t, J=6 Hz, CH$_2$), 1.94 (2H, qt, J=6.5 Hz, CH$_2$), 3.95 (2H, t, J=6.5 Hz, NCH$_2$), 4.39 (2H, q, J=7 Hz, OCH$_2$), 10.3 (1H, s, OH); $^{13}$C NMR (CDCl$_3$, 125.8 Hz) δ ppm: 14.16, 15.34, 29.79, 35.01, 37.63, 45.03, 62.44, 125.21, 147.23, 155.28, 158.89, 169.55; HRMS (ESI) calcd for C$_{13}$H$_{19}$N$_2$O$_4$(M+H) 267.1345, found 267.1352.

EXAMPLE 4

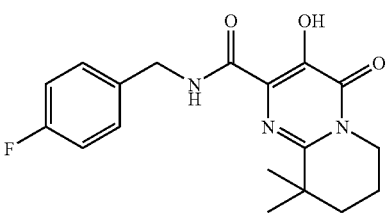

3-Hydroxy-9,9-dimethyl-4-oxo-6,7,8,9-tetrahydro-4H-pyrido[1,2-a]pyrimidine-2-carboxylic acid 4-fluoro-benzylamide. The title compound was prepared from intermediate 11 and 4-fluorobenzyl amine using Method A. $^1$H NMR (CDCl$_3$, 500 MHz) δ ppm: 1.31 (6H, s, CH$_3$), 1.70–1.74 (2H, m, CH$_2$), 1.91–1.99 (2H, m, CH$_2$), 3.96 (2H, t, J=6.3 Hz, NCH$_2$), 4.56 (2H, d, J=6.2 Hz, CH$_2$), 7.02 (2H, t, J=8.6 Hz, Ar—H), 7.29 (2H, dd, J=5 Hz, 8.7 Hz, Ar—H), 7.87 (1H, brt, J=~5 Hz, NH), 11.7 (1H, s, OH). $^{13}$C NMR (CDCl$_3$, 125.8 Hz) δ ppm: 18.54, 30.05, 34.87, 37.43, 42.41, 44.97, 115.77, 115.94, 125.38, 129.36, 129.43, 133.35, 145.90, 155.46, 158.85, 161.46, 163.42, 168.58. HRMS (ESI) calcd for C$_{18}$H$_{21}$FN$_3$O$_3$ (M+H) 346.1567, found 346.1552.

Intermediate 12

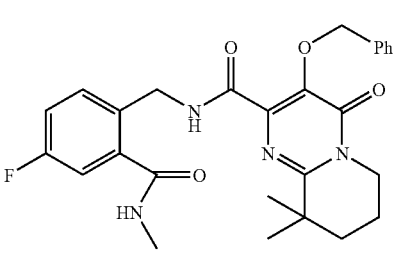

N-(4-Fluoro-2-(methylcarbamoyl)benzyl)-3-(benzyloxy)-9,9-dimethyl-4-oxo-6,7,8,9-tetrahydro-4H-pyrido[1,2-a]pyrimidine-2-carboxamide. The title compound was prepared from 3-(benzyloxy)-9,9-dimethyl-4-oxo-6,7,8,9-tetrahydro-4H-pyrido[1,2a]pyrimidine-2-carboxylic acid (prepared via from intermediate 11) and intermediate 3, 2-aminomethyl-5-fluoro-N-methyl-benzamide trifluoroacetic acid according to Method B. $^1$H NMR (300 MHz, CDCl$_3$) δ ppm: 1.38 (6 H, s) 1.70–1.78 (2 H, m) 1.90–2.00 (2 H, m) 2.95 (3 H, d, J=4.8 Hz) 3.92 (2 H, t, J=6.2 Hz) 4.51 (2 H, d, J=6.6 Hz) 5.20 (2 H, s) 6.80 (1 H, s) 6.97–7.07 (1 H, m) 7.11 (1 H, dd, J=9.0, 2.7 Hz) 7.25–7.31 (3 H, m) 7.38 (1 H, dd, J=8.6, 5.3 Hz) 7.48 (2 H, dd, J=7.3, 2.2 Hz) 8.50 (1 H, t, J=6.8 Hz); LC/MS m/z 493 (M+H).

EXAMPLE 5

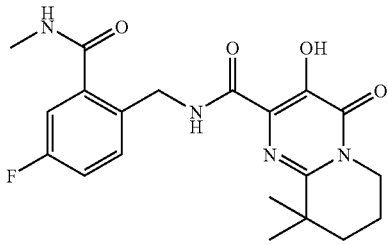

N-(4-Fluoro-2-(methylcarbamoyl)benzyl)-3-hydroxy-9,9-dimethyl-4-oxo-6,7,8,9-tetrahydro-4H-pyrido[1,2-a]pyrimidine-2-carboxamide. Intermediate 12, N-(4-fluoro-2-(methylcarbamoyl)benzyl)-3-(benzyloxy)-9,9-dimethyl-4-oxo-6,7,8,9-tetrahydro-4H-pyrido[1,2-a]pyrimidine-2-carboxamide was treated with trifluoroacetic acid, according to Method D to provide the title compound. $^1$H NMR (300 MHz, CDCl$_3$) δ ppm: 11.76 (1 H, br), 8.84 (1 H, t, J=5.9 Hz), 7.46 (1 H, dd, J=8.4, 5.5 Hz), 7.04–7.18 (2 H, m), 6.22 (1 H, s), 4.57 (2 H, d, J=6.6 Hz), 3.93 (2 H, t, J=6.4 Hz), 3.00 (3 H, d, J=4.8 Hz), 1.88–2.00 (2 H, m), 1.67–1.74 (2 H, m), 1.33–1.39 (6 H, m); HRMS (ESI) calcd for C$_{20}$H$_{24}$FN$_4$O$_4$ (M+H) 403.1782, found 403.1783.

Intermediate 13

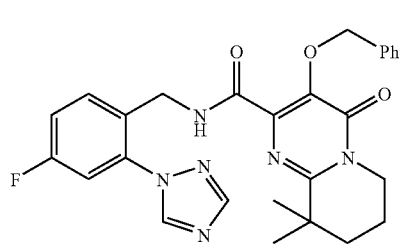

N-(4-Fluoro-2-(1H-1,2,4-triazol-1-yl)benzyl)-3-(benzyloxy)-9,9-dimethyl-4-oxo-6,7,8,9-tetrahydro-4H-pyrido[1,2-a]pyrimidine-2-carboxamide. The title compound was prepared from 3-(benzyloxy)-9,9-dimethyl-4-oxo-6,7,8,9-tetrahydro-4H-pyrido[1,2a]pyrimidine-2-carboxylic acid (prepared via from intermediate 11) and intermediate 2, (4-fluoro-2-(1H-1,2,4-triazol-1-yl)phenyl)methanamine hydrochloride) according to Method B. $^1$H NMR (300 MHz, CDCl$_3$) δ ppm: 1.39 (13 H, s) 1.91–2.03 (2 H, m) 3.92 (2 H, t, J=6.4 Hz) 4.40 (2 H, d, J=6.6 Hz) 5.23 (2 H, s) 7.04(1 H, dd, J=8.8, 2.6 Hz) 7.09–7.19(1 H, m) 7.24–7.34(3 H, m) 7.52(2 H, dd, J=7.9, 1.7 Hz) 7.71 (1 H, dd, J=8.6, 6.0 Hz) 8.06 (1 H, s) 8.37 (1 H, s) 8.60 (1 H, t, J=6.8 Hz); LC/MS m/z 503 (M+H).

EXAMPLE 6

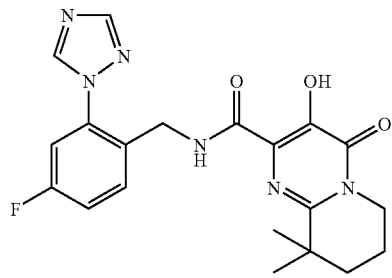

N-(4-Fluoro-2-(1H-1,2,4-triazol-1-yl)benzyl)-3-hydroxy-9,9-dimethyl-4-oxo-6,7,8,9-tetrahydro-4H-pyrido[1,2-a]pyrimidine-2-carboxamide. Intermediate 13, N-(4-fluoro-2-(1H-1,2,4-triazol-1-yl)benzyl)-3-(benzyloxy)-9,9-dimethyl-4-oxo-6,7,8,9-tetrahydro-4H-pyrido[1,2-a]pyrimidine-2-carboxamide was treated with trifluoroacetic acid, according to Method D to provide the title compound. $^1$H NMR (300 MHz, CDCl$_3$) δ ppm: 11.66 (1H, br), 8.88 (1H, t, J=6.2 Hz), 8.44 (1H, s), 8.18 (1H, s), 7.67 (1H, dd, J=8.4, 5.9 Hz), 7.18 (1H, dt, J=8.2, 2.6 Hz), 7.09 (1H, dd, J=8.4, 2.6 Hz), 4.43 (2H, d, J=7.0 Hz), 3.95 (2H, t, J=6.4 Hz), 1.88–2.00 (2H, m), 1.69–1.76 (2H, m), 1.37 (6H, s); HRMS (ESI) calcd for C$_{20}$H$_{22}$FN$_6$O$_3$ (M+H) 413.1737, found 413.1719.

EXAMPLES 7–10

Intermediate 14

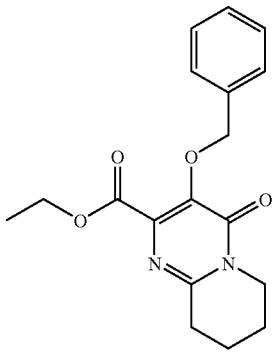

Ethyl 3-benzyloxy-4-oxo-6,7,8,9-tetrahydro-4H-pyrido[1,2-a]pyrimidine-2-carboxylate. Diethyl oxalate (7.66 g, 52.4 mmol) and ethyl benzyloxyacetate (10.2 g, 52.5 mmol) in dry tetrahydrofuran (70 ml) were treated at 22° C. with sodium hydride (2.31 g of a 60% dispersion in mineral oil, 57.7 mmol) and ethanol (40 μl). The tetrahydrofuran was then evaporated under reduced pressure and the residue treated with a mixture of 2-iminopiperidine hydrochloride (7.05 g, 52.2 mmol) in a solution of sodium ethoxide (26.0 mmol, prepared from 0.60 g of sodium) in ethanol (70 ml) and the resulting mixture heated at 60° C. for 4 h. Acetic acid (2 ml) was added and the ethanol was evaporated under reduced pressure. The residue was diluted with ethyl acetate washed successively with saturated sodium bicarbonate and brine, dried over anhydrous magnesium sulfate and concentrated under reduced pressure. Chromatography on silica gel (elution toluene/ethyl acetate 1:1) gave 2.37 g (14% yield) of the title ester as white crystals; mp 97–99° C. (ethyl acetate-hexane). $^1$HNMR 400 MHz (CDCl$_3$) δ (ppm): 1.33 (3H, t, J=7.1 Hz, CH$_3$), 1.92 (2H, m, CH$_2$), 2.0 (2H, m, CH$_2$), 2.97 (2H, t, J=6.8 Hz, CH$_2$), 4.02 (2H, t, J=6.3 Hz, NCH$_2$), 4.36 (2H, q, J=7.1 Hz, OCH$_2$), 5.27 (2H, s, OCH$_2$), 7.3–7.51 (5H, m, aromatics). Anal. Calcd for C$_{18}$H$_{20}$N$_2$O$_4$: C, 65.84; H, 6.14; N, 8.53. Found: C 65.72, H 6.33, N 8.41.

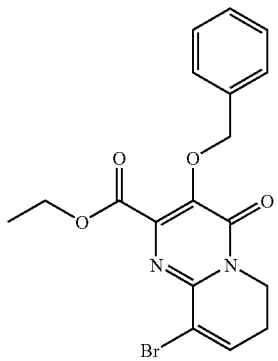

Intermediate 15

Ethyl 3-(benzyloxy)-9-bromo-4-oxo-6,7-dihydro-4H-pyrido[1,2-a]pyrimidine-2-carboxylate. A mixture intermediate 14, ethyl 3-benzyloxy-4-oxo-6,7,8,9-tetrahydro-4H-pyrido[1,2-a]pyrimidine-2-carboxylate, (1.00 g, 3.05 mmol) and sodium acetate (1.50 g) in acetic acid (20 ml) was heated at 120° C. and then treated with a solution of bromine (1.5 g, 9.2 mmol) in acetic acid (5 ml). After 1 h at 120° C., the reaction mixture was cooled and concentrated in vacuo. The residue was diluted with ethyl acetate, washed with water and brine and dried over anhydrous magnesium sulfate. Evaporation of the solvent and chromatography of the residue on silica gel (elution gradient of ethyl acetate in hexane) gave 0.531 g (43% yield) of the title material as a white solid. $^1$HNMR 400 MHz (CDCl$_3$) δ (ppm): 1.34 (3H, t, J=7.1 Hz, CH$_3$), 2.60 (2H, m, CH$_2$), 4.28 (2H, t, J=7.3 Hz, CH$_2$), 4.38 (2H, q, J=7.1 Hz, OCH$_2$), 5.34 (2H, s, OCH$_2$), 7.05 (1H, t, J=4.8 Hz, CH), 7.3–7.52 (5H, m, aromatics).

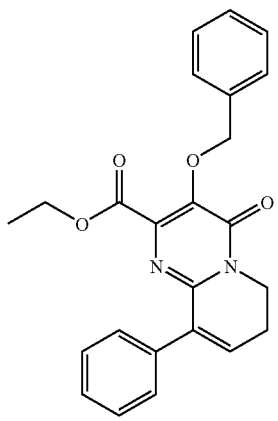

Intermediate 16

Ethyl 3-(benzyloxy)-4-oxo-9-phenyl-6,7-dihydro-4H-pyrido[1,2-a]pyrimidine-2-carboxylate. A mixture of intermediate 15, ethyl 3-(benzyloxy)-9-bromo-4-oxo-6,7-dihydro-4H-pyrido[1,2-a]pyrimidine-2-carboxylate, (0.477 g, 1.18 mmol) in acetonitrile (15 ml) and water (15 ml) was treated with phenylboronic acid (0.190 g, 1.53 mmol), sodium carbonate (0.275 g, 2.6 mmol) and tetrakis(triphenylphosphine)palladium(0) (0.200 g). The reaction mixture was degassed, flushed with argon and heated at 90° C. for 30 min. The reaction mixture was then concentrated in vacuo, diluted with ethyl acetate, washed with water and brine, dried over anhydrous magnesium sulfate and concentrated. Chromatography of the residue on silica gel (elution gradient of ethyl acetate in hexane) gave 0.325 g (68% yield) of the title material as a clear oil. $^1$HNMR 400 MHz (CDCl$_3$) δ (PPM): 1.26 (3H, t, J=7.1 Hz, CH$_3$), 2.68 (2H, m, CH$_2$), 4.27 (2H, q, J=7.1 Hz, OCH$_2$), 4.32 (2H, t, J=7.6 Hz, CH$_2$), 5.34 (2H, s, OCH$_2$), 6.73 (1H, t, J=4.8 Hz, CH), 7.3–7.55 (10H, m, aromatics). HRMS (ESI$^+$) calculated for C$_{24}$H$_{23}$N$_2$O$_4$ [M+H$^+$]: 403.1658; found: 403.1659.

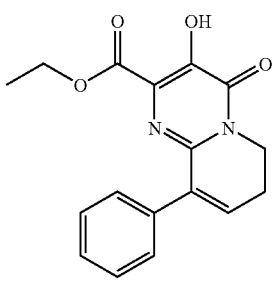

Intermediate 17

Ethyl 3-hydroxy-4-oxo-9-phenyl-6,7-dihydro-4H-pyrido[1,2-a]pyrimidine-2-carboxylate. A solution of intermediate 16, ethyl 3-(benzyloxy)-4-oxo-9-phenyl-6,7-dihydro-4H-pyrido[1,2-a]pyrimidine-2-carboxylate (0.320 g, 0.80 mmol) in dichloromethane (5 ml) was treated with trifluoroacetic acid (5 ml) and the resulting mixture was stirred at 25° C. for 16 h. The reaction mixture was then concentrated in vacuo and the residue was triturated with ether to give 0.189 g (76% yield) of the title material as a white solid; mp 151° C. $^1$HNMR 400 MHz (CDCl$_3$) δ (ppm): 1.37 (3H, t, J=7.1 Hz, CH$_3$), 2.67 (2H, m, CH$_2$), 4.34 (2H, t, J=7.1 Hz, CH$_2$), 4.37 (2H, q, J=7.1 Hz, OCH$_2$), 6.70 (1H, t, J=4.8 Hz, CH), 7.38 (3H, m, aromatics), 7.55 (2H, m, aromatics), 10.70 (1H, s, OH). HRMS (ESI$^+$) calculated for C$_{17}$H$_{17}$N$_2$O$_4$ [M+H$^+$]: 313.1188; found: 313.1181.

EXAMPLE 7

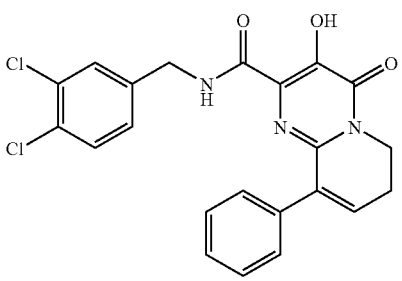

N-(3,4-Dichlorobenzyl)-3-hydroxy-4-oxo-9-phenyl-6,7-dihydro-4H-pyrido[1,2-a]pyrimidine-2-carboxamide. The title compound was prepared from intermediate 17 and 3,4-dichlorobenzyl amine using Method A. $^1$HNMR 400 MHz (CDCl$_3$) δ (ppm): 2.69 (2H, m, CH$_2$), 4.34 (2H, t, J=7.1 Hz, CH$_2$), 4.45 (2H, d, J=6.6 Hz, CH$_2$), 6.67 (1H, t, J=4.8 Hz, CH), 7.06 (1H, dd, J=2.0 Hz and J=8.1 Hz, aromatic), 7.31 (1H, d, J=2.0 Hz, aromatic), 7.32–7.39 (5H, m, aromatics), 7.43 (1H, d, J=8.1 Hz, aromatic), 7.58 (1H, broad, NH), 11.86 (1H, s, OH). HRMS (ESI$^+$) calculated for C$_{22}$H$_{18}$Cl$_2$N$_3$O$_3$ [M+H$^+$]: 442.0725; found: 442.0714.

EXAMPLE 8

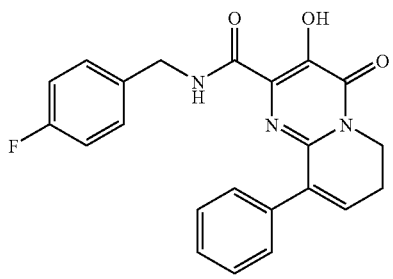

N-(4-Fluorobenzyl)-3-hydroxy-4-oxo-9-phenyl-6,7-dihydro-4H-pyrido[1,2-a]pyrimidine-2-carboxamide. The title compound was prepared from intermediate 17 and 4-fluorobenzyl amine using Method A. $^1$HNMR 400 MHz (CDCl$_3$) δ (ppm): 2.68 (2H, m, CH$_2$), 4.33 (2H, t, J=7.1 Hz, CH$_2$), 4.46 (2H, d, J=6.1 Hz, CH$_2$), 6.65 (1H, t, J=4.8 Hz, CH), 7.05 (2H, m, aromatics), 7.19 (2H, m, aromatics), 7.27–7.38 (5H, m, aromatics), 7.56 (1H, broad, NH), 11.98 (1H, s, OH). HRMS (ESI$^+$) calculated for C$_{22}$H$_{19}$FN$_3$O$_3$ [M+H$^+$]: 392.1410; found: 392.1399.

EXAMPLE 9

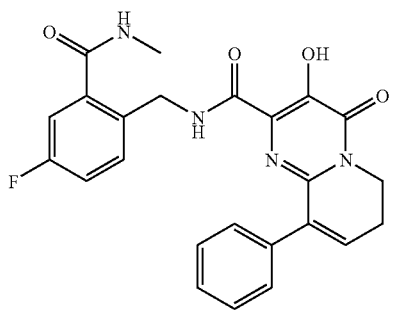

N-(4-Fluoro-2-(methylcarbamoyl)benzyl)-3-hydroxy-4-oxo-9-phenyl-6,7-dihydro-4H-pyrido[1,2-a]pyrimidine-2-carboxamide. The title compound was prepared from intermediate 16 and intermediate 3 using the methods described above. $^1$HNMR 400 MHz (CDCl$_3$) δ (ppm): 2.66 (2H, m, CH$_2$), 2.94 (3H, d, J=5.1 Hz, CH$_3$), 4.32 (2H, t, J=7.1 Hz, CH$_2$), 4.53 (2H, d, J=6.6 Hz, CH$_2$), 6.17 (1H, broad q, NH), 6.64 (1H, t, J=4.8 Hz, CH), 7.11 (1H, dd, J=2.5 Hz and J=8.0 Hz, aromatic), 7.15 (1H, dd, J=2.5 Hz and J=8.8 Hz, aromatic), 7.36–7.48 (6H, m, aromatics), 8.31 (1H, broad t, NH), 12.21 (1H, s, OH). HRMS (ESI$^+$) calculated for C$_{24}$H$_{22}$FN$_4$O$_4$ [M+H$^+$]: 449.1625; found: 449.1618.

EXAMPLE 10

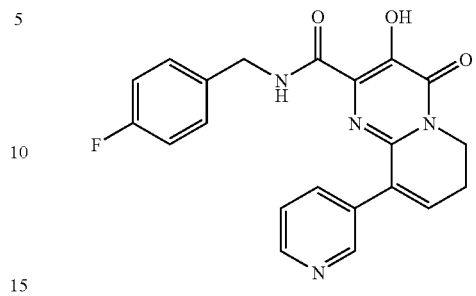

N-(4-Fluorobenzyl)-3-hydroxy-4-oxo-9-(pyridin-3-yl)-6,7-dihydro-4H-pyrido[1,2-a]pyrimidine-2-carboxamide. $^1$HNMR 400 MHz (DMSO-d$_6$) δ (ppm): 2.69 (2H, m, CH$_2$), 4.14 (2H, t, J=6.8 Hz, CH$_2$), 4.41 (2H, d, J=6.1 Hz, CH$_2$), 7.01 (1H, t, J=4.8 Hz, CH), 7.17 (2H, m, aromatics), 7.29 (2H, m, aromatics), 7.74 (1H, dd, J=5.0 Hz and J=8.1 Hz, aromatic), 8.28 (1H, d, J=8.1 Hz, aromatic), 8.49 (1H, broad t, NH), 8.73 (1H, d, J=5.0 Hz, aromatic), 8.84 (1H, s, aromatic), 12.34 (1H, s, OH). HRMS (ESI$^+$) calculated for C$_{21}$H$_{18}$FN$_4$O$_3$ [M+H$^+$]: 393.1363; found: 393.1366.

EXAMPLE 11

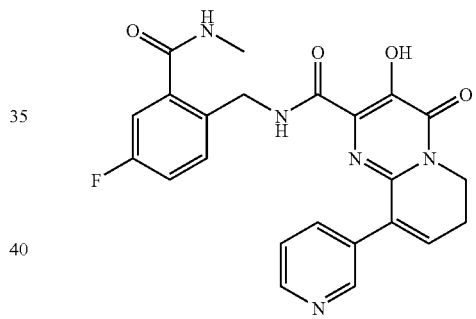

N-(4-Fluoro-2-(methylcarbamoyl)benzyl)-3-hydroxy-4-oxo-9-(pyridin-3-yl)-6,7-dihydro-4H-pyrido[1,2-a]pyrimidine-2-carboxamide. $^1$HNMR 400 MHz (DMSO-d$_6$) δ (ppm): 2.60 (2H, m, CH$_2$), 2.74 (3H, d, J=4.5 Hz, CH$_3$), 4.12 (2H, t, J=7.0 Hz, CH$_2$), 4.44 (2H, d, J=6.5 Hz, CH$_2$), 6.75 (1H, broad, NH), 7.2–7.4 (4H, m, aromatics), 7.92 (1H, m, aromatic), 8.51 (2H, m, aromatics), 8.59 (1H, s, aromatic), 12.33 (1H, s, OH). HRMS (ESI$^+$) calculated for C$_{23}$H$_{21}$FN$_5$O$_4$ [M+H$^+$]: 450.1578; found: 450.1566.

EXAMPLE 12

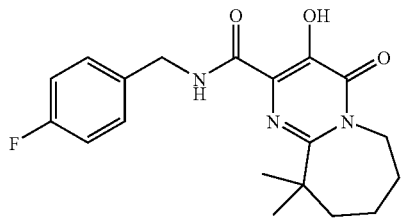

N-(4-Fluorobenzyl)-3-hydroxy-10,10-dimethyl-4-oxo-4,6,7,8,9,10-hexahydropyrimido[1,2-a]azepine-2-carboxamide. $^1$H NMR (500 MHz, CDCl$_3$) δ ppm: 1.39 (s, 6), 1.72 (br m, 6), 4.49 (br s, 2), 4.57 (d, 2), 7.05 (m, 2), 7.31 (m, 2), 7.86 (br m, 1), 11.75 (s, 1).

EXAMPLE 13

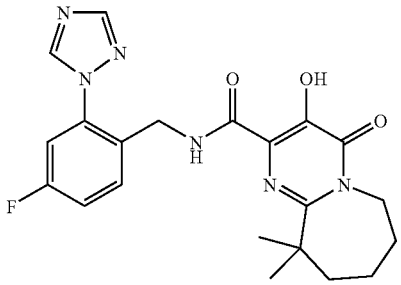

N-(4-Fluoro-2-(1H-1,2,4-triazol-1-yl)benzyl)-3-hydroxy-10,10-dimethyl-4-oxo-4,6,7,8,9,10-hexahydropyrimido[1,2-a]azepine-2-carboxamide. $^1$H NMR (500 MHz, CDCl$_3$) δ ppm: 1.47 (s, 6), 1.73 (br m, 6), 4.44 (br m, 4), 7.11 (m, 1), 7.20 (m, 1), 7.71 (m, 1), 8.15 (s, 1), 8.45 (s, 1), 8.91 (br m, 1), 11.78 (s, 1).

We claim:
1. A compound of Formula I

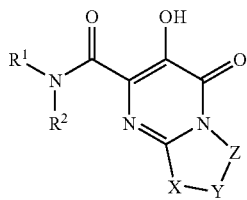

wherein:
R$^1$ is C$_{1-6}$(Ar$^1$)alkyl;
R$^2$ is hydrogen, hydroxy, C$_{1-6}$alkyl, or C$_{1-6}$alkoxy;
R$^3$ is hydrogen, halo, hydroxy, cyano, C$_{1-6}$alkyl, C$_{1-6}$haloalkyl, C$_{1-6}$alkoxy, C$_{1-6}$haloalkoxy, CON(R$^6$)(R$^6$), NHCOR$^6$, or Ar$^2$;
R$^4$ is hydrogen, halo, hydroxy, cyano, C$_{1-6}$akyl, C$_{1-6}$alkoxy, C$_{1-6}$haloalkyl, or C$_{1-6}$haloalkoxy;
R$^5$ is hydrogen, halo, hydroxy, cyano, C$_{1-6}$alkyl, C$_{1-6}$alkoxy, C$_{1-6}$haloalkyl or C$_{1-6}$haloalkoxy;
R$^6$ is hydrogen or C$_{1-6}$alkyl;
R$^7$ is C$_{1-6}$alkyl;
Ar$^1$ is

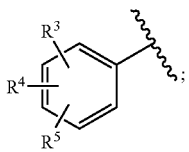

Ar$^2$ is tetrazolyl, triazolyl, pyrazolyl, imidazolyl, pyrrolyl, or dioxothiazinyl, and is substituted with 0–2 substituents selected from the group consisting of amino, oxo, halo, and C$_{1-6}$alkyl;
Ar$^3$ is phenyl or pyridinyl substituted with 0–2 substituents selected from halo, C$_{1-6}$alkyl, and C$_{1-6}$alkoxy; and
X—Y—Z is C(R$^7$)$_2$CH$_2$CH$_2$, C(R$^7$)$_2$CH$_2$CH$_2$CH$_2$, C(R$^7$)$_2$CH$_2$CH$_2$CH$_2$CH$_2$, C(Ar$^3$)=CHCH$_2$, C(Ar$^3$)=CHCH$_2$CH$_2$, or C(Ar$^3$)=CHCH$_2$CH$_2$CH$_2$;
or a pharmaceutically acceptable salt thereof.

2. A compound of claim 1 where R$^1$ is

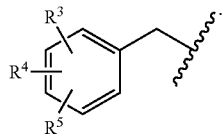

3. A compound of claim 1 where R$^1$ is

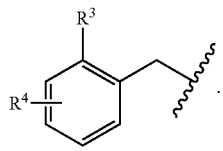

4. A compound of claim 1 where R$^2$ is hydrogen.
5. A compound of claim 1 where R$^3$ is hydrogen, chloro, flouro, methyl, or NHCOR$^6$; R$^4$ is hydrogen, chloro, flouro, or methyl; and R$^5$ is hydrogen.
6. A compound of claim 1 where R$^3$ is triazolyl substituted with 0–1 methyl groups; R$^4$ is hydrogen, chloro, flouro, or methyl; and R$^5$ is hydrogen.
7. A compound of claim 1 where R$^6$ is hydrogen or methyl.
8. A compound of claim 1 where R$^7$ is methyl.
9. A compound of claim 1 where X—Y—Z is C(R$^7$)$_2$CH$_2$CH$_2$, C(R$^7$)CH$_2$CH$_2$CH$_2$, or C(R$^7$)$_2$CH$_2$CH$_2$CH$_2$CH$_2$.
10. A compound of claim 1 where X—Y—Z is C(Ar$^3$)=CHCH$_2$, C(Ar$^3$)=CHCH$_2$CH$_2$, or C(Ar$^3$)=CHCH$_2$CH$_2$CH$_2$.
11. A compound of claim 1 selected from the group consisting of
N-(4-Fluorobenzyl)-3-hydroxy-8,8-dimethyl-4-oxo-4,6,7,8-tetrahydropyrrolo[1,2-a]pyrimidine-2-carboxamide,
N-(4-Fluoro-2-(methylcarbamoyl)benzyl)-3-hydroxy-8,8-dimethyl-4-oxo-4,6,7,8-tetrahydropyrrolo[1,2-a]pyrimidine-2-carboxamide;
N-(4-fluoro-2-(1H-1,2,4-triazol-1-yl)benzyl)-3-hydroxy-8,8-dimethyl-4-oxo-4,6,7,8-tetrahydropyrrolo[1,2-a]pyrimidine-2-carboxamide;
3-Hydroxy-9,9-dimethyl-4-oxo-6,7,8,9-tetrahydro-4H-pyrido[1,2-a]pyrimidine-2-carboxylic acid 4-fluorobenzylamide;
N-(4-Fluoro-2-(methylcarbamoyl)benzyl)-3-hydroxy-9,9-dimethyl-4-oxo-6,7,8,9-tetrahydro-4H-pyrido[1,2-a]pyrimidine-2-carboxamide;
N-(4-Fluoro-2-(1H-1,2,4-triazol-1-yl)benzyl)-3-hydroxy-9,9-dimethyl-4-oxo-6,7,8,9-tetrahydro-4H-pyrido[1,2-a]pyrimidine-2-carboxamide;
N-(3,4-Dichlorobenzyl)-3-hydroxy-4-oxo-9-phenyl-6,7-dihydro-4H-pyrido[1,2-a]pyrimidine-2-carboxamide;
N-(4-Fluorobenzyl)-3-hydroxy-4-oxo-9-phenyl-6,7-dihydro-4H-pyrido[1,2-a]pyrimidine-2-carboxamide;

N-(4-Fluoro-2-(methylcarbamoyl)benzyl)-3-hydroxy-4-oxo-9-phenyl-6,7-dihydro-4H-pyrido[1,2-a]pyrimidine-2-carboxamide;

N-(4-Fluorobenzyl)-3-hydroxy-4-oxo-9-(pyridin-3-yl)-6,7-dihydro-4H-pyrido[1,2-a]pyrimidine-2-carboxamide;

N-(4-Fluoro-2-(methylcarbamoyl)benzyl)-3-hydroxy-4-oxo-9-(pyridin-3-yl)-6,7-dihydro-4H-pyrido[1,2-a]pyrimidine-2-carboxamide;

N-(4-Fluorobenzyl)-3-hydroxy-10,10-dimethyl-4-oxo-4,6,7,8,9,10-hexahydropyrimido[1,2-a]azepine-2-carboxamide; and N-(4-Fluoro-2-(1H-1,2,4-triazol-1-yl)benzyl)-3-hydroxy-10,10-dimethyl-4-oxo-4,6,7,8,9,10-hexahydropyrimido[1,2-a]azepine-2-carboxamide;

or a pharmaceutically acceptable salt thereof.

12. A composition comprising a therapeutic amount of a compound of claim 1 and a pharmaceutically acceptable carrier.

13. A method for treating HIV infection comprising administering a therapeutically effective amount of a compound of claim 1, or a pharmaceutically acceptable salt thereof, to a patient in need thereof.

14. The method of claim 13, further comprising a therapeutically effective amount of one or more other HIV treatment agents selected from the group consisting of HIV protease inhibitors, HIV nucleoside reverse transcriptase inhibitors, HIV non-nucleoside reverse transcriptase inhibitors, HIV-entry inhibitors, HIV integrase inhibitors, immunomodulators, or a combination thereof.

* * * * *

UNITED STATES PATENT AND TRADEMARK OFFICE
CERTIFICATE OF CORRECTION

PATENT NO.         : 7,173,022 B2
APPLICATION NO.    : 11/138773
DATED              : February 6, 2007
INVENTOR(S)        : B. Narasimhulu Naidu et al.

It is certified that error appears in the above-identified patent and that said Letters Patent is hereby corrected as shown below:

Column 40, line 41:

$C(R^7)CH_2CH_2CH_2$ should read $C(R^7)_2CH_2CH_2CH_2$

Signed and Sealed this

Tenth Day of April, 2007

JON W. DUDAS
*Director of the United States Patent and Trademark Office*